(12) United States Patent
Fowler

(10) Patent No.: US 6,309,388 B1
(45) Date of Patent: Oct. 30, 2001

(54) SYMMETRIC CONIZATION ELECTROCAUTERY DEVICE

(75) Inventor: Robert Stuart Fowler, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/470,789

(22) Filed: Dec. 23, 1999

(51) Int. Cl.[7] ................................................. A61B 18/18
(52) U.S. Cl. ............................................. 606/45; 600/564
(58) Field of Search ............................. 606/41, 45, 47, 606/49; 600/564

(56) References Cited

U.S. PATENT DOCUMENTS

| | | | | |
|---|---|---|---|---|
| 3,357,422 | * | 12/1967 | Creelman | 606/167 |
| 3,628,522 | * | 12/1971 | Kato | 606/167 |
| 3,943,916 | * | 3/1976 | Vadas | 128/304 |
| 4,887,593 | * | 12/1989 | Wiley et al. | 606/45 |
| 5,032,124 | * | 7/1991 | Menton | 606/14 |
| 5,047,042 | * | 9/1991 | Jerath | 606/167 |
| 5,554,159 | * | 9/1996 | Fischer | 606/45 |
| 5,676,663 | * | 10/1997 | Kim | 606/45 |
| 5,810,807 | * | 9/1998 | Ganz et al. | 606/47 |
| 5,951,550 | * | 9/1999 | Shirley et al. | 606/45 |
| 6,017,339 | * | 1/2000 | Sadamasa | 606/46 |
| 6,066,132 | * | 5/2000 | Chen et al. | 606/28 |
| 6,176,858 | * | 1/2001 | Dequesne et al. | 606/45 |

* cited by examiner

Primary Examiner—Linda C. M. Dvorak
Assistant Examiner—David M. Ruddy
(74) Attorney, Agent, or Firm—Gregory F. Cotterell

(57) ABSTRACT

The present invention goes to a tissue electrocautery device that accommodates anatomical structures lying at more than one longitudinal axes. Such a circumstance is encountered when attempting to perform symmetric tissue electrocautery of an endocervical canal where the longitudinal axis of the vaginal vault is at an angle to the longitudinal axis of the endocervical canal. The device of the present invention uses a hollow housing, elongate along a first longitudinal axis, having a proximal portion with a proximal end and a distal end, and includes a distal portion from the distal end. The distal portion is elongate along a second longitudinal axis and pivotable in relation to the proximal portion at a selectable angle to the first longitudinal axis. Within the housing is a rotatable electrically conducting mechanism, adapted to conduct electrocautery energy from an electrode proximal to the housing proximal portion to a coupling proximate the distal portion, while rotating the coupling with a removable handle proximal to the housing proximal portion. The electrical energy is delivered to an electrocautery head, carrying an electrocautery wire, operably electrically engageable with the coupling and rotatable around a longitudinal axis parallel the second longitudinal axis, electrocauterizing tissue of a human patient while rotating around its longitudinal axis.

27 Claims, 3 Drawing Sheets

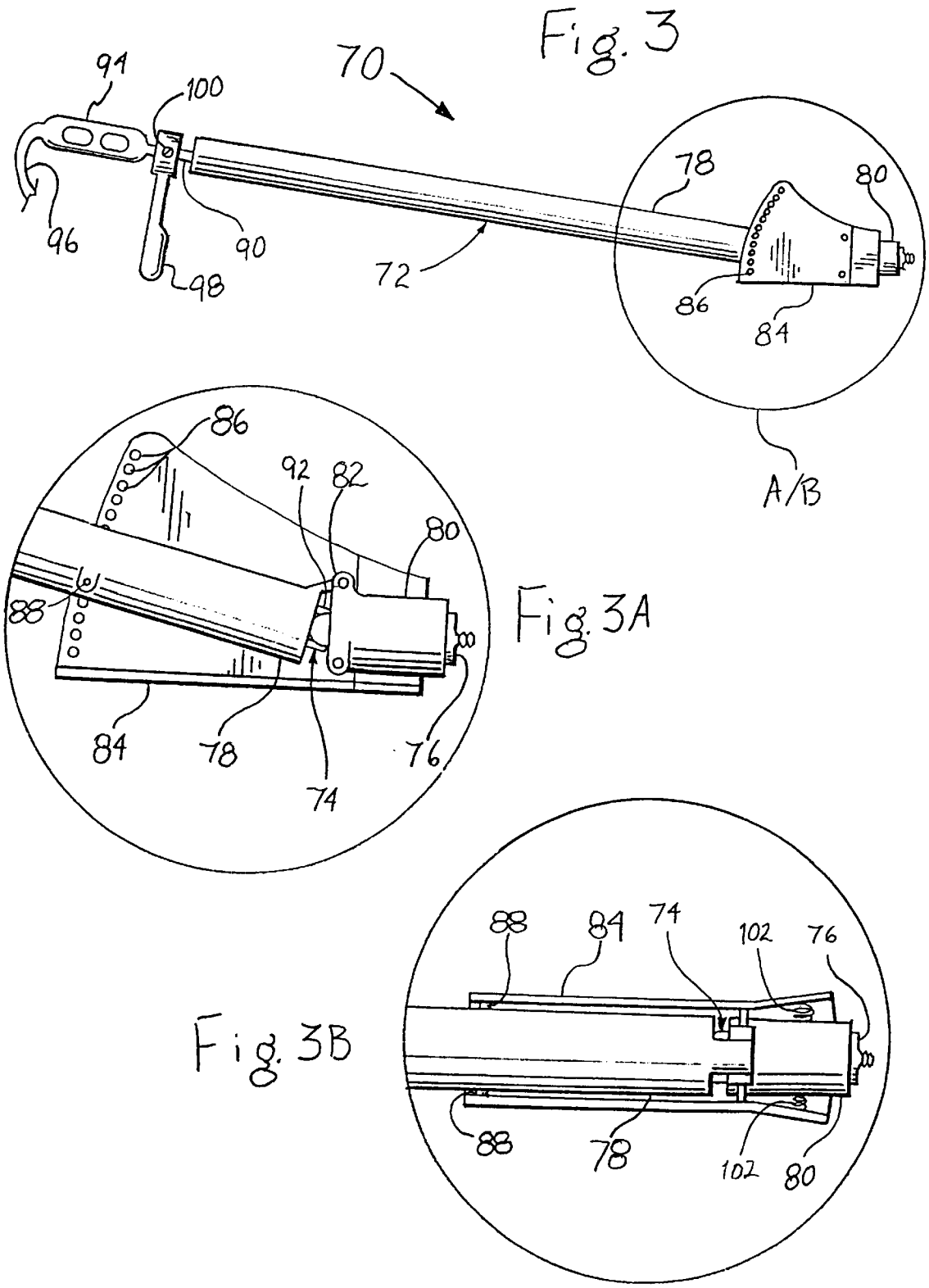

SYMMETRIC CONIZATION ELECTROCAUTERY DEVICE

FIELD OF THE INVENTION

The present invention discloses a device for electrocautery of tissue, in particular, for an improved electrocautery for performing a symmetric conization, and more particular, a device for performing electrocautery conization of a uterine cervix.

BACKGROUND OF THE PRESENT INVENTION

In medicine, biopsying a sample of tissue remains the gold standard for pursuing a diagnosis of tissue pathology. The biopsied tissue is then examined histologically for evidence of dysplasia and cancerous transformation to yield the diagnosis.

The treatment of choice, particularly in the women of childbearing age, for cervical dysplasia involving the cervical canal or for more than one degree of discrepancy between the degree of dysplasia represented on the Pap smear versus colposcopic directed biopsy is conization of the cervix. In a conization of the cervical tissue, the traditional cold knife procedure involved removing a cone shaped tissue specimen from the cervix with the axis of the cone centered on the axis of the endocervical canal. The cone base is positioned at the external cervical os, oriented with the cone apex toward the internal cervical os. With the advent of electrocautery devices the specimen shape may be refined to a more anatomically directed biopsy specimen that maintains a more accurate depth of surgical resection but seldom resembles an actual cone. There are a number of methods and devices for performing this procedure.

The ideal endocervical biopsy yields a cylinder of tissue approximately two centimeters in length and five to seven mm deep on all faces centered on the axis of the endocervical canal. Seldom is the ideal achieved, but there are several methods available. First, surgically excise the tissue. Surgical excision, i.e., cold knife conization, is accomplished with a conventional scalpel.

Second, use a loop electrosurgical excision procedure (LEEP) to first create a superficial excision followed by a second deeper excision extending further along the endocervical canal toward the internal cervical os. The loop excision uses a loop of wire for electrocautery excision of the specimen. The loop is handheld with the first pass depth less than two centimeters, consequently, the need for more than one pass in order to approach the ideal endocervical treatment depth.

Third, use a modified LEEP electrode that is shaped to combine the superficial and deep excisions into one pass. The modified LEEP conization electrodes consist of an insulated stiff rod with a wire electrode extending from the tip of the rod to a cross arm, which approximates the configuration of a cone specimen.

A fourth method uses $CO_2$ laser energy in lieu of a scalpel for performing an excisional cervical conization.

Sharp excision techniques using devices such as a scalpel, have the advantage for controlled tissue removal and minimal tissue injury with preservation of resection margins for clarity of histologic analysis, but the procedure has poor anatomic control. A drawback to cold knife conization excision over LEEP is the increased blood loss from the wound edge. Because of their size, including the handle, scalpels are more difficult to wield in the closer confines of the vaginal vault. A number of devices for mounting, holding, and modifying scalpel blades have been developed, but these devices have proven to be either difficult to keep the excision centered or difficult to turn while in the vaginal vault.

LEEP has improved blood loss control, but the straight stiff rods are difficult to use within the confines of the vaginal vault because of the angle differences between the long axis of the vaginal vault to the long axis of the endocervical canal. The difficulty in obtaining proper alignment of the device to the axis of the endocervical canal leads to off centered and or tilted excisions that run a significant risk of only partially excising abnormal tissue, completely missing the abnormal tissue, and or removing excessive amounts of normal tissue.

What is needed is a device that is capable of concentrically removing cervical tissue around the endocervical axis of rotation at an appropriate biopsy depth with minimal blood loss and minimal injury to cervical margin tissues.

SUMMARY OF THE INVENTION

The present invention is an improved device for symmetric electrocautery removal of tissue of a human patient. The device comprises a hollow housing, an electrocautery head and a mechanism for rotating the electrocautery head while conducting electricity to the electrocautery head.

The housing is elongate along a first longitudinal axis and has a proximal portion, the proximal portion having a proximal end and a distal end. The hollow housing may also have a distal portion, which has a second longitudinal axis, and is distal to the distal end of the proximal portion. This second longitudinal axis is at a selectable angle to the first longitudinal axis.

The rotating mechanism is operably engageable within the hollow housing along the first and second longitudinal axes and is adapted to conduct electrocautery energy from an electrode proximate to the housing proximal portion proximal end to a coupling proximate the distal end of the first portion or proximate the distal portion, if the distal portion is used. The rotating mechanism ends in a coupling that is aligned along the second longitudinal axis. The rotating mechanism rotates the coupling with a removable handle proximate the proximal end of the housing.

The present invention anticipates several different types of rotating mechanisms. In one embodiment, the rotating mechanism uses a flexible cable, preferably metal, or at least electrically conducting. The flexible cable may be single strand or multi-strand as either a braid or a coil.

The electrocautery head carries an electrocautery wire and is operably and electrically engageable with the coupling and rotatable around the second longitudinal axis. When electrocautery energy is delivered to the electrocautery head, the rotating mechanism rotates the electrocautery head about the second longitudinal axis, symmetrically electrocauterizing tissue of a human patient about that second longitudinal axis. The present invention anticipates that the electrocautery head is removable and replaceable with different styles, shapes and configurations for the body and the wire.

The present invention anticipates several conformations for the housing. Where only a proximal portion for the housing, is used, the present invention may use either a flexible cable or a U-joint for completing the bend and aligning the electrocautery head with the endocervical canal. With this arrangement, it is preferable to use an electrocautery head that has an extended tip for maintaining alignment and orientation of the electrocautery head with the endocervical canal.

Where a proximal portion and a distal portion are used for the housing, preferably a flexible hinge joins these two portions. The hinge may be friction fit to provide for some movement when sufficiently forced, but readily maintaining a selected angle when not forced to move. Alternatively, the present invention contemplates a locking mechanism using a bracket pivotably mounted to the distal portion and having a more proximal end that may operable engage the housing proximal portion. Preferably, the bracket includes two halves shaped to provide for shielding from possible electrical energy exposure at the hinge area and provide for selectable angular movement of the proximal portion with respect to the distal portion. The engagement of the bracket with the proximal portion may be with nibs engaging detents, a ratchet and pawl, interdigitating teeth, or similar engaging mechanisms.

The bracket is preferably spring biased relative to the distal portion for holding the bracket in the locking position with the proximal portion. Squeezing the bracket halves against the spring bias pivots the bracket in relation to the distal portion and releases the bracket from the proximal portion. While released the angle of the proximal portion in relation to the distal portion may be selected, with the selectable angle having a range from about 0° to about 70°.

An object of the present invention is to provide an electrocautery device capable of being conveniently held by an operator with the proximal housing of the device having a first longitudinal axis align with a first orientation and while symmetrically electrocauterizing a "cone" of tissue about a second orientation having a second longitudinal axis at an angle to the first longitudinal axis. Electrocauterization is provided by rotating the electrocautery head with a rotating mechanism with the housing alignable with the first and second orientations.

Another object of the present invention is to provide an electrocautery device capable of bending through a range of operator selectable angles between the first longitudinal axis and the second longitudinal axis.

An additional object of the present invention is to provide an electrocautery device having an adjustable locking mechanism that locks the device at the operator selected angles. The locking mechanism may additionally serve the purpose of providing safety by shielding the patient from inadvertently touching the rotating mechanism at the level of the angle between the first and second longitudinal axes.

These and other objects of the present invention and many of the attendant advantages of the present invention will be readily appreciated as the same become better understood by reference to the following detailed description when considered in connection with the accompanying drawings.

BRIEF DESCRIPTION OF THE DRAWINGS

FIG. 3 is a side elevational view an additional alternative embodiment of the present invention depicting an alternative mechanism for holding a user selectable angle of bend in the housing;

FIG. 3A is an enlarged partial sectional side elevational view of the circled portion of FIG. 3, in which the near side portion of the mechanism for holding an angle has been removed; and FIG. 3B is an enlarged partial sectional top view of the circled portion of FIG. 3.

DETAILED DESCRIPTION OF THE PRESENT INVENTION

Figure 1:
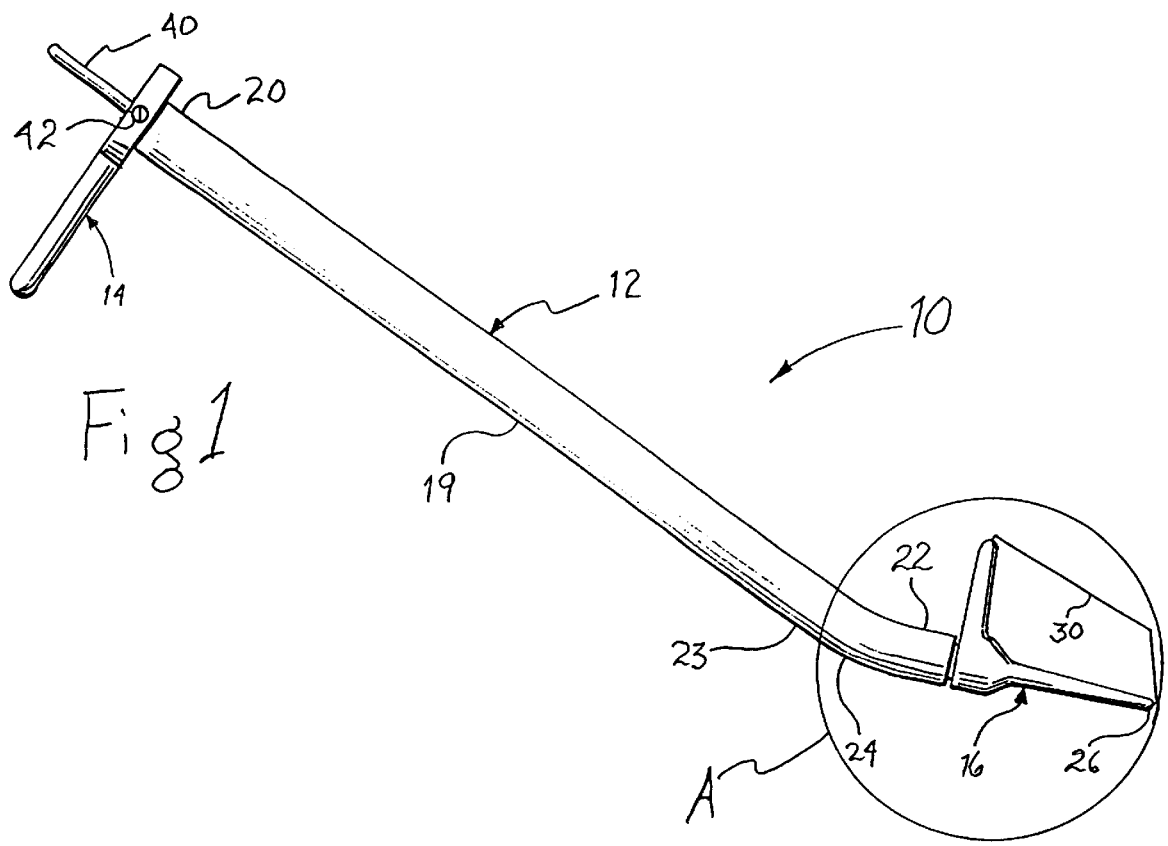
FIG. 1 is a side elevational view of an embodiment of the present invention.
Figure 1A:
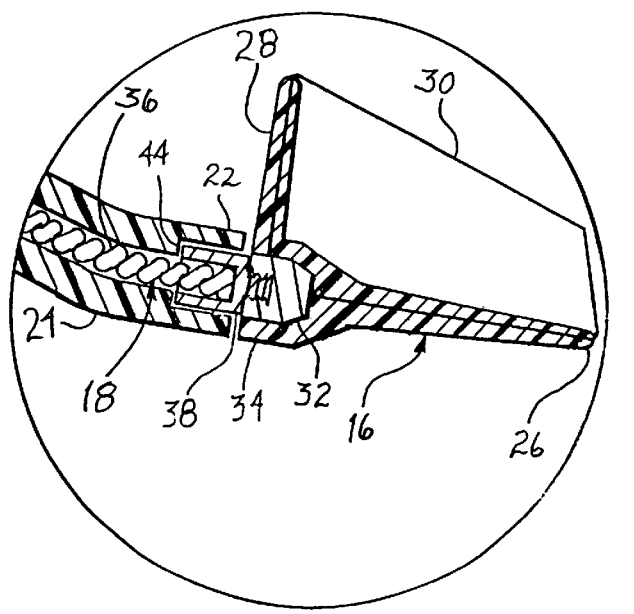
FIG. 1A is an enlarged partial elevational cross-sectional view of the circled portion of FIG. 1.

Embodiments of the present invention are depicted in the various Figures, wherein like numbers reference similar structures throughout the various figures. An embodiment of the present invention is depicted in FIGS. 1 and 1A. In FIGS. 1 and 1A, there is depicted a symmetric electrocautery tissue conization device 10 comprising a housing 12, a rotation handle 14 slidably engaging housing 12, an electrocautery head 16, and a rotating subassembly 18 operably attached to electrocautery head 16 distally and operably coupled to rotation handle 14 proximally.

Housing 12 includes a proximal portion 19 having a proximal end 20 and a distal end 23 along its longitudinal axis, and incorporates a bend 24 positioned between proximal portion 19 and a distal portion 22. In a first embodiment, housing 12 is an elongated cylinder of rigid material having the added characteristic of being a good electrical insulator. A number of materials are suitable for use in the housing and include, without limitation, plastics, ceramics, and natural and synthetic rubber compounds. There are a number of plastics known in the art that are useful in this capacity. Examples are acrylics, methaclylics, poly-vinyl-chloride, polypropylene, polyethylene, polystyrene, polyurethane, polytetrafluoroethylene, and their copolymer. Preferably the plastic is biocompatible, as well as, sterilizable using standard sterilization techniques known in the medical arts. Metals are not excluded from use as the housing for the present invention, but as will be evident, because the present invention uses electrocautery, the operator must take other precautions in order to protect the patient from inadvertent application of the electrical energy.

The purpose of bend 24 is to provide appropriate access and alignment of the device, in particular, aligning electrocautery head 16 to the patient's external cervical os and endocervical canal while still providing alignment of the more proximal housing with the patient's vaginal vault. The uterine cervix projects into the vaginal vault anywhere from an anteverted/anteflexed position to a retroverted/retroflexed position, with the long axis of the endocervical canal typically angled relative to the long axis of the vaginal vault. With proximal end 20 and rotation handle 14 remaining outside the vaginal introitus for the operator to hold and manipulate the device, bend 24 accommodates version/flexion to position electrocautery head 16 at the external cervical os with the long axis of electrocautery head 16 in alignment with the long axis of the endocervical canal while maintaining the orientation of the more distal portion of housing 12 with the long axis of the vaginal vault. The present invention anticipates providing a set of similar devices, the set having a range of selectable angles, each unit having a different degree of angulation at bend 24. The present invention anticipates that the angle of bend 24 may range from 0° to 70°.

Electrocautery head 16 is designed to have its longitudinal axis align with that of the longitudinal axis of the endocervical canal. Electrocautery head 16 ends in a distal tip 26 and has a side arm 28 extending laterally from its more proximal base 34. An electrocautery wire 30 extends from distal tip 26 to side arm 28. Electrocautery head 16 is manufactured from electrically insulating material, such as plastics, glass, various rubbers, and ceramics. As with housing 12, there are a number of materials suitable for use as electrocautery head 16. These materials include, without limitation, plastics such as acrylics, methacrylics, poly-vinyl-chloride, polyethylene, polypropylene, polystyrene, polyurethane, polytetrafluoroethylene, and their copolymers. Preferably the material is biocompatible, as well as, capable of withstanding sterilization techniques used in the medical arts. Electrocautery head 16 is constructed so that electrocautery wire 30 is only exposed from the end of side arm 28 to distal tip 26 with the remainder of the electrocautery wire traveling within the body of electrocautery head 16. Electrocautery wire 30 completes an electrical connection with a coupling 32 at base 34 of electrocautery head 16.

Rotating subassembly 18 comprises a cable body 36 having a distal coupling mechanism 38 and a proximal electrode 40. Rotating subassembly 18 traverses through the hollow center of housing 12. Proximal electrode 40 is operably and releasably connected to rotation handle 14 by telescopically sliding rotation handle 14 over proximal electrode 40 and locking rotation handle 14 to proximal electrode 40 with use of a set screw 42. The side of rotation handle 14 closest to proximal end 20 of housing 12 is positioned to closely abut and be in slidable contact with proximal end 20. At distal portion 22 of housing 12, rotating subassembly 18 ends in a distal coupling mechanism 38. Distal portion 22 is constructed with a counter bore 44, which provides a shoulder to operably interact with coupling mechanism 38. To assemble, cable 36 is threaded through the hollow center of housing 12 from distal portion 22 to proximal end 20 until distal coupling mechanism 38 abuts counter bore 44. Then rotation handle 14 is slipped over proximal electrode 40 until its body slidably abuts against proximal end 20. This positioning is secured with set screw 42. To diminish friction between rotation handle 14 and housing 12, and between distal coupling mechanism 38 and housing 12, a number of techniques may be used such as surgical lubricants and jellies, polytetrafluoroethylene washers and the like (not shown). Friction is not anticipated to be much of a problem given the slow rotational speeds used by an operator with the present invention.

Electrocautery head 16 is then attached to rotating subassembly 18. To attach electrocautery head 16 to rotating subassembly 18, coupling 32 is complementary to coupling mechanism 38 so that coupling 32 may be threaded onto coupling mechanism 38. Alternatively, the complementary shapes of coupling 32 and coupling mechanism 38 may be of any number of shapes and configurations, such as, square, hex, or star drives, for example. In these alternative arrangements, a set screw may be used to secure coupling 32 to coupling mechanism 38. Regardless of style of coupling, the coupling of electrocautery head 16 to rotating subassembly 18 must also be electrical in nature.

Rotation handle 14 may be constructed from any number of materials that are electrically insulating. Examples of such materials are, but not limited to, plastics, rubbers and ceramics. Examples of several plastics are acrylics, methacrylics, poly-vinyl-chloride, polyethylene, polypropylene, polystyrene, polyurethane, polytetrafluoroethylene, and their copolymers. Rotation handle 14 is adapted for grasping by an operator to apply a rotational force to the rotation handle while the operator is holding onto housing 12.

Rotating subassembly 18 is electrically conducting. Distal coupling mechanism 38 is electrically coupled with coupling 32 of electrocautery head 16. As a consequence, electrocautery wire 30 is electrically connected to proximal electrode 40 upon coupling electrocautery head 16 to rotating subassembly 18. Cable 36 may be, in fact, a single strand of material or multiple strands as are depicted in the Figures. Cable 36 may be constructed from any number of metals and metal alloys, such as, but not limited to, steel, iron, nickel, copper, chrome, silver, tin, and nickel/titanium. Nickel/titanium has a distinct advantage over other metals and metal alloys because of its superelastic characteristics. As a superelastic material, nickel/titanium more easily withstands repetitive rotational and bending movements without undue strain and fatigue that result, ultimately, in failure of other materials. Nickel/titanium is useful as a single strand or multi-strand, having superior elastic characteristics. However, stainless steel is another ideal alloy for use in the present invention considering its cost vs. strength benefits. Either coiled or braided, appropriately prepared stainless steel can withstand considerable repetitive bending and rotation before any noticeable fatigue is encountered.

Other ways arc available with the present invention for accomplishing the equivalent of the bend. In an alternative embodiment, depicted in FIG. 2, housing 12, with fixed bend 24, of the previous embodiment is replaced with a housing 50 having a proximal main body 52 linked to a smaller distal sleeve 54 at hinge 56. Hinge 56 provides for adjusting the bend in housing 50 to any desired angle. The remainder of main body 52 would be similar to the more proximal portion of housing 12 seen in FIG. 1.

Hinge 56 is suited with sufficient friction to maintain any desired angle. In the example shown in FIG. 2, tensioning a screw 58 may control friction in hinge 56. The long axis of distal sleeve 54 is angled in relation to the long axis of main body 52 to align the long axis of distal sleeve 54 to the long axis of the endocervical canal while maintaining alignment of the long axis of main body 52 with the long axis of the vaginal vault. A cautery head (not shown) is attachable to a rotating subassembly 60, in this instance using a cable with a threaded end coupling, which is then properly centerable and alignable with the long axis of the endocervical canal. It should be readily apparent to those skilled in this art that appropriate shielding is needed over the hinged area proximate angle gap 57 to guard the patient against inadvertent exposure to electrical energy from an exposed rotating subassembly.

Figure 2:
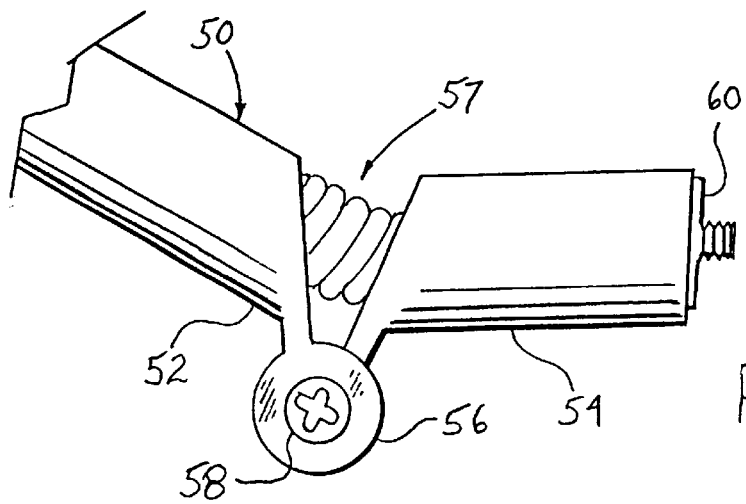
FIG. 2 is a side elevational view of a section of an alternative embodiment of the present invention depicting a hinged housing.

A hinged device could replace an entire set of devices having fixed bends, such as the device depicted in FIG. 1. Such an embodiment, preferred over the previous embodiment, is shown in FIGS. 3, 3A, and 3B wherein the hinged housing may use either a flexible cable subassembly or a U-joint subassembly. The advantage of a U-joint is the joint's ability to hold a range of degrees of angulation with greater efficiency in transferring torque forces while cutting compared to a cable or a single strand of flexible material. Such an embodiment is shown in FIGS. 3, 3A, and 3B, wherein device 70 comprises a housing 72, and a rotation subassembly 74 using the threaded version of a coupling 76. Rotation subassembly 74 preferably uses a U-joint joining two rigid shafts within housing 72. However, the present invention also anticipates the use of a flexible cable as shown in FIGS. 1 and 2, or a single strand of flexible metal.

Housing 72 includes a rigid main portion 78 connected to a rigid smaller portion 80 by a hinge 82. An angle locking bracket 84 is pivotally attached to portion 80 and operably engages main portion 78, primarily at detent holes 86 with complementary raised nubs 88 on the side of main portion 78. Hinge 82 is capable of rotating from at least 0° to 70° of angle. Alternatively, this arrangement could be reversed with two holes in opposite sides of main portion 78 and a series of complementary raised nubs on bracket 84. Alternatively, a ratchet and pawl, interdigitating teeth, or similar arrangement may also be used to set and hold the angle (not shown). Selection of the angle would depend entirely on the degree of version and flexion of the cervix and endocervical canal in relation to the vaginal vault.

Rotational subassembly 74 includes a first rigid shaft 90, rotatable within main portion 78 of housing 72, and operably connected to coupling 76 through a U-joint 92. Coupling 76 is rotatable within portion 80 of housing 72 through a second rigid shaft connecting U-joint 92 to coupling 76. First rigid shaft 90, coupling 76, the second rigid shaft and U-joint 92 are electrically conductive, with coupling 76 electrically connectable to any suitable electrocautery head. A switch 94 and power supply cable 96 are electrically attached to the opposite end of first rigid shaft 90. A handle 98 is slidably positioned and attached to a proximal position on first rigid shaft 90, secured by a set screw 100, with handle 98 abutting and operably engaging the end of main portion 78.

Angle locking bracket 84 serves dual functions in that it provides the ability to hold the desire angle of housing 72 and also provides electrical shielding about the area of the hinge where U-joint 92 would otherwise be exposed to the patient. A set of springs 102, positioned between the halves of angle locking bracket 84 and portion 80 and are biased to hold angle locking bracket 84 and its detent holes 86 in operable contact with raised nubs 88 of main portion 78. Compression force against springs 102 provides for pivoting of angle locking bracket 84 at its pivotable attachment with portion 80, releasing the engaged detent holes 86 from raised nubs 88. While holding angle locking bracket with the springs in compression, the angle at hinge 82 may be changed to any desired setting with the range of the hinge and the angle locking bracket. The present invention anticipates that this selectable operable range of angles would extend from 0° to about 70°.

A number of insulating materials are suitable for use in angle locking bracket 84 and include, without limitation, plastics, ceramics, and natural and synthetic rubber compounds. There are a number of plastics known in the art that are useful in this capacity. Examples are acrylics, methacrylics, poly-vinyl-chloride, polypropylene, polyethylene, polystyrene, polyurethane, polytetrafluoroethylene, and their copolymers. Preferably the plastic is biocompatible, as well as, sterilizable using standard sterilization techniques known in the medical arts.

Figure 4:
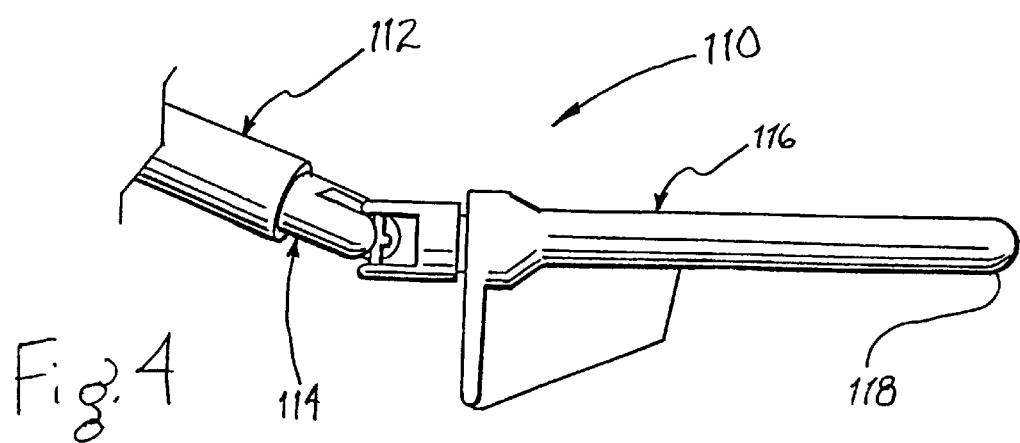
FIG. 4 is a side elevational view of a section of another additional alternative embodiment of the present invention depicting another type of cutting head and a U-joint coupling in lieu of a housing bend for the present invention.

Another modification that may be used in conjunction with a U-joint is depicted in FIG. 4 as device 110, which includes a housing 112, a rotational subassembly 114 and an electrocautery head 116. The difference with device 110 is the absence of a smaller portion connected to housing 112 with a hinge, and the addition of a tip extension 118 to electrocautery head 116. Because there is no smaller portion to the housing to stabilize device 110 in the long axis of an endocervical canal, tip extension 118 is provided and is intended to fit snuggly further up the patient's endocervical canal. This tip extension 118 holds electrocautery head 116 in proper orientation to the long axis of an endocervical canal. The more snug the fit, the better the endocervical canal will tend to hold tip extension 118, and the rest of electrocautery head 116, on the longitudinal axis of the endocervical canal and maintain the centering of electrocautery head 116. Preferably, the diameter of tip extension 118 is about 4 mm or less, but may range from less than 1 mm to more than about 8 mm. Extension 118 may be an integral part of electrocautery head 116, as depicted, or alternatively, it may be a removable extension (not shown) that can be snapped on or screwed on.

In operation, and referring to FIGS. 1 and 1A, an operator selects device 10 having the appropriate degree of bend at bend 24. The selection on an appropriate device 10 is predicated on the degree of version/flexion of the endocervical canal in relation to the longitudinal axis of the vagina encountered at the time of surgery. Although not shown, the patient is grounded to an appropriate electrocautery energy source and the other electrode of the source is connected to proximal electrode 40. With the electrical continuity within device 10, electrocautery wire 30 now becomes the working electrode of the energy source. While grasping housing 12, distal tip 26 is brought proximate to the center of the external cervical os and the longitudinal axis of electrocautery head 16 is aligned with the long axis of the endocervical canal. While supplying electrocautery energy to device 10, the operator then inserts electrocautery head 16 through the external cervical os and into the endocervical canal with electrocautery wire 30 cutting into the side wall of the cervical opening. Still grasping housing 12, the operator also grasps rotation handle 14 and turns the handle around the longitudinal axis of proximal portion of housing 12. This rotational movement is translated through rotating subassembly 18 to electrocautery head 16, which is rotated about the longitudinal axis of the endocervical canal. This rotation sweeps electrocautery wire 30 through a 360° arc performing a symmetric conization of the cervical canal. As the wire cuts, it also cauterizes and provides a clean margin of resection preserving a good sample for histologic examination.

Device 10 may be disassembled for convenient cleaning and resterilization. Electrocautery head 16, in the alternative, may be disposable. In disassembly, handle 14 is removed from electrode 40 and subassembly 18 may slide distally through housing 12. Alternatively, a set screw or pin (not shown) may be used to set coupling mechanism 38 to cable 36. To disassemble, this set screw or pin may be released and coupling mechanism 38 removed from cable 36 and cable 36 withdrawn proximally.

Device 70 of FIGS. 3, 3A, and 3B may be operated in a similar fashion to device 10. The salient feature distinguishable with device 70 is the use of housing 72 with hinge 82 and angle locking bracket 84. The selection of the appropriate angle with which to perform the conization is readily set with device 70 by compressing the two halves of angle locking bracket 84 against the bias of springs 102. As the halves of angle locking bracket 84 pivot, nibs 88 are disengaged from detent hole 86 and hinge 82 is now free to pivot. The appropriate angle between housing main portion 78 longitudinal axis and portion 80 longitudinal axis is determined as before by aligning the axis of portion 80 to the long axis of the endocervical canal and the aligning the axis of main portion 78 with the long axis of the vaginal vault. When alignment is complete, the bias of springs 102 is released and the angle is locked into place by the appropriate detents 86 engaging nibs 88. Device 70 may now be operated similar to device 10 for electrocautery conization of the endocervical canal. For illustrative purposes, device 70 is depicted with switch 94 near rotation handle 98 for ready access to control of the electrocautery energy. However, the present invention anticipates that control may be conveniently placed on the floor as a foot switch operated by the surgeon, or elsewhere and operated by other personnel in the operating room at the direction of the surgeon.

Device 70 also may be disassembled for convenient cleaning and resterilization. In disassembly, housing 72 is positioned so main portion 78 is axially aligned with portion 80. Then handle 98 and switch 94 are removed from rigid shaft 90 and rotational subassembly 74 may slide distally through housing 72.

The foregoing description is considered as illustrative only of the principles of the invention, and since numerous modifications and changes will readily occur to those skilled in the art, it is not the inventor's desire to limit the invention to the exact construction and operation shown and described herein. Accordingly, all suitable modifications and equivalents may be resorted to, falling within the scope of the present invention.

I claim:

1. An improved device for electrocautery removal of tissue of a human patient, the device comprising:
   a hollow housing, elongate along a first longitudinal axis, having a proximal portion with a proximal end and a distal end;
   rotating means, operably engageable within the housing along the first longitudinal axis and adapted to conduct electrocautery energy from an electrode proximate to the housing proximal portion to a coupling proximate the distal end and extendable beyond the distal end along a second longitudinal axis at an angle to the first longitudinal axis, for rotating the coupling with a removable handle proximate the proximal end of the housing; and
   an electrocautery head, carrying an electrocautery wire, operably electrically engageable with the coupling and rotatable around the second longitudinal axis, electrocauterizing tissue of a human patient while rotating around its longitudinal axis.

2. The device of claim 1 wherein the housing further includes a distal portion from the distal end, elongate along the second longitudinal axis.

3. The device of claim 2 wherein the proximal portion and distal portion of the housing are integrated as one piece joined by a bend in the housing, and the rotating means includes a flexible cable from the electrode to the coupling.

4. The device of claim 3 wherein the housing comprises a synthetic polymer.

5. The device of claim 4 wherein the synthetic polymer is selected from a list of polymers consisting of: acrylic, methacrylic, poly-vinyl-chloride, polyethylene, polypropylene, polystyrene, polyurethane, and polytetrafluoroethylene.

6. The device of claim 5 wherein the synthetic polymer is a copolymer of at least two synthetic polymers selected from a list of polymers consisting of: acrylic, methacrylic, poly-vinyl-chloride, polyethylene, polypropylene, polystyrene, polyurethane, and polytetrafluoroethylene.

7. The device of claim 2 wherein the proximal portion and distal portion of the housing are integrated as one piece joined by a bend in the housing, and the rotating means includes a flexible wire from the electrode to the coupling.

8. The device of claim 2 wherein the proximal portion and distal portion are joined by a hinge.

9. The device of claim 8 further including an angle locking subassembly, the angle locking subassembly including a bracket having means for engaging and locking the proximal portion and pivotably engaging the distal portion, the engaging means including at least one spring operably engaged between the bracket and the distal portion biasing the bracket toward operably engaging the proximal portion.

10. The device of claim 8 wherein the rotating means includes a flexible cable from the electrode to the coupling.

11. The device of claim 8 wherein the rotating means includes a flexible wire from the electrode to the coupling.

12. The device of claim 8 wherein the rotating means includes a first shaft and a second shaft joined by a U-joint at the level of the hinge from the electrode to the coupling.

13. The device of claim 1 wherein the rotating means includes a flexible cable from the electrode to the coupling.

14. The device of claim 1 wherein the rotating means includes a flexible wire from the electrode to the coupling.

15. The device of claim 1 wherein the rotating means includes a first shaft and a second shaft joined by a U-joint and extends from the electrode to the coupling.

16. The device of the 1 wherein the electrocautery head further comprises an extension beyond the distal most extent of the electrocautery wire, the extension having a longitudinal axis coaxial with the second longitudinal axis.

17. An improved device for electrocautery removal of tissue of a human patient, the device comprising:
   a hollow housing, elongate along a first longitudinal axis, having a proximal portion with a proximal end and a distal end, and includes a distal portion operably engaging the proximal portion from the distal end, the distal portion elongate along a second longitudinal axis and pivotable in relation to the proximal portion at a selectable angle to the first longitudinal axis;
   rotating means, operably engageable within the housing along the first longitudinal axis and the second longitudinal axis, and adapted to conduct electrocautery energy from an electrode proximal to the housing proximal portion to a coupling proximate the distal portion, for rotating the coupling with a removable handle proximal to the housing proximal portion; and
   an electrocautery head, carrying an electrocautery wire, operably electrically engageable with the coupling and rotatable around the second longitudinal axis, electrocauterizing tissue of a human patient while rotating around its longitudinal axis.

18. The device of claim 17 further including an angle locking subassembly, the angle locking subassembly including a bracket having means for engaging and locking the proximal portion and pivotably engaging the distal portion, with at least one spring operably engaged between the bracket and the distal portion biasing the bracket toward operably engaging the proximal portion with the engaging means.

19. The device of claim 17 wherein the rotating means includes a flexible cable from the electrode to the coupling.

20. The device of claim 17 wherein the rotating means includes a flexible wire from the electrode to the coupling.

21. The device of claim 17 wherein the rotating means includes a first shaft and a second shaft joined by a U-joint and extends from the electrode to the coupling.

22. The device of claim 17 wherein the housing proximal portion and distal portion are pivotable at a hinge.

23. The device of claim 22 further including an angle locking subassembly, the angle locking subassembly including a bracket having means for engaging and locking the proximal portion and pivotably engaging the distal portion, with at least one spring operably engaged between the bracket and the distal portion biasing the bracket toward operably engaging the proximal portion with the engaging means.

24. The device of claim 22 wherein the rotating means includes a flexible cable from the electrode to the coupling.

25. The device of claim 22 wherein the rotating means includes a flexible wire from the electrode to the coupling.

26. The device of claim 22 wherein the rotating means includes a first shaft and a second shaft joined by a U-joint at the level of the hinge and extends from the electrode to the coupling.

27. The device of claim 26 further including an angle locking subassembly, the angle locking subassembly including a bracket having means for engaging and locking the proximal portion and pivotably engaging the distal portion, with at least one spring operably engaged between the bracket and the distal portion biasing the bracket toward operably engaging the proximal portion with the engaging means.

* * * * *